United States Patent
Estevez Pintado et al.

(10) Patent No.: US 10,314,772 B2
(45) Date of Patent: Jun. 11, 2019

(54) UV-FILTERS, METHOD OF PRODUCING THE SAME AND THEIR USE IN COMPOSITIONS, IN PARTICULAR SUNSCREENS

(71) Applicant: UNIVERSIDADE CATÓLICA PORTUGUESA, Oporto (PT)

(72) Inventors: Maria Manuela Estevez Pintado, Oporto (PT); Paula Castro, Oporto (PT); Clara Piccirillo, Oporto (PT)

(73) Assignee: UNIVERSIDADE CATOLICA PORTUGUESA, Oporto (PT)

(*) Notice: Subject to any disclaimer, the term of this patent is extended or adjusted under 35 U.S.C. 154(b) by 0 days.

(21) Appl. No.: 15/323,559

(22) PCT Filed: Jul. 2, 2015

(86) PCT No.: PCT/IB2015/055001
§ 371 (c)(1),
(2) Date: Jan. 3, 2017

(87) PCT Pub. No.: WO2016/001871
PCT Pub. Date: Jan. 7, 2016

(65) Prior Publication Data
US 2017/0119636 A1 May 4, 2017

(30) Foreign Application Priority Data
Jul. 2, 2014 (PT) ........................................ 107747

(51) Int. Cl.
*A61K 8/24* (2006.01)
*A61Q 17/04* (2006.01)
*A61K 8/06* (2006.01)

(52) U.S. Cl.
CPC ................ *A61K 8/24* (2013.01); *A61K 8/064* (2013.01); *A61Q 17/04* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 2004/0170582 A1 | 9/2004 | Harivel | |
| 2009/0074645 A1 | 3/2009 | Wu et al. | |
| 2012/0014891 A1* | 1/2012 | Rastrelli | A61K 8/24 424/60 |
| 2012/0321578 A1* | 12/2012 | Leuridan | A61K 8/0229 424/63 |

FOREIGN PATENT DOCUMENTS

| | | |
|---|---|---|
| JP | H0525458 A | 2/1993 |
| WO | 9701304 A1 | 1/1997 |
| WO | 2010109400 A2 | 9/2010 |

OTHER PUBLICATIONS de Araujo, T., Journal of Physics: Conference Series 249: 02102 (2010).*
Ereiba, K., et al., Journal of Biophysical Chemistry 4(4): 122-130 (2013).*
Brezova et al. "Photoactivity of mechanochemically prepared nanoparticulate titanium dioxide investigated by EPR spectroscopy." J. of Photochemistry and Photobiology A: Chemistry vol. 206, (2009), pp. 177-187.
Clark. "A Stopped-Flow Kinetics Experiment for Advanced Undergraduate Laboratories: Formation of Iron(III) Thiocyanate." J. of Chemical Education, vol. 74, No. 10, Oct. 1997, pp. 1214-1217.
Dondi et al. "Pseudobrookite ceramic pigments: Crystal structural, optical and technological properties." Solid State Sciences vol. 9, (2007), pp. 362-369. ScienceDirect www.sciencedirect.com.
Garoli et al. "Effectiveness of different substrate materials for in vitro sunscreen tests." J. of Dermatological Science, vol. 56, (2009), pp. 89-98.
Garoli et al. "Sunscreen tests: Correspondence between in vitro data and values reported by the manufacturers." J. of Dermatological Science, vol. 52, (2008), pp. 193-204.
International Search Report for International Patent Application No. PCT/IB2015/055001 dated Oct. 26, 2015. 3 pages.
Larson et al. "General Structure Analysis System (GSAS)." Los Alamos National Laboratory Report LAUR 86-748 (2004), 231 pages.
Springsteen, et al. "In vitro measurement of sun protection factor of sunscreens by diffuse transmittance." Analytica Chimica Acta, vol. 380, (1999), p. 155-164.
Tampieri et al. "Intrinsic magnetism and hyperthermia in bioactive Fe-doped hydroxyapatite." Acta Biomaterialia, vol. 8, (2012), pp. 843-851.
Tiano et al. "Modified TiO2 particles differentially affect human skin fibroblasts exposed to UVA light." Free Radical Biology & Medicine, vol. 49, (2010), pp. 408-415.
Toby. "EXPGUI, a graphical user interface for GSAS." J. of Applied Crystallography, vol. 34, (2001), pp. 210-213. ISSN 0021-00898.
Tupker et al. "Guidelines on sodium lauryl sulfate (SLS) exposure tests." Contact Dermatitis, vol. 37, (1997), pp. 53-69. ISSN 0105-1873.
Velasco et al. "Broad spectrum bioactive sunscreens." Int. J. of Pharmaceutics, vol. 363, (2008), pp. 50-57.
Wu et al. "A novel biomagnetic nanoparticle based on hydroxyapatite." Nanotechnology, IOP, Bristol, GB, (Apr. 25, 2007), vol. 18, No. 16. 9 pages. DOI:10.1088/0957-4484/18/16/165601, ISSN 0957-4484, p. 165601, XP020119043.

* cited by examiner

*Primary Examiner* — David J Blanchard
*Assistant Examiner* — Daniel F. Coughlin
(74) *Attorney, Agent, or Firm* — Leason Ellis LLP (57) ABSTRACT

The present disclosure relates to new UV-filters, method of producing the same and their use in compositions in particular, cosmetic/pharmaceutical or textile compositions, namely sunscreens cream or sunscreens textile article, in particular the present disclosure relates to hydroxyapatite based-compound comprising $Ca_9FeH(PO_4)_7$ and/or $\alpha$-Fe2O3 in hematite form for use in a method for protecting the skin against UV radiation.

12 Claims, 7 Drawing Sheets

Fig 8 ly used in commercial sunscreens: both compounds provide protection over the whole UV range. Literature data show that using these compounds in the form of nanoparticles improves their effectiveness, leading to an enhanced protection. At the same time, however, there is concern about the possible toxicity of the nanoparticles; although several studies were published on the subject, to date there is no incontestable evidence on this topic. For $TiO_2$ and ZnO use, however, another possible risk is associated with their photocatalytic properties under UV and visible light. Both minerals are in fact photochemically reactive compounds; this means that, under irradiation, they can form free radicals and other reactive species that can cause some of the health problems associated with UV exposure. Scientific studies, for instance, showed that the formation of radical species can occur for ZnO-containing sunscreens under illumination, and such reactive species could potentially be as dangerous for the skin as much as the UV light itself. Small $TiO_2$ particles have also been shown to have serious effects on mitochondrial function, altering 85 biochemical metabolites, many of which are associated with the cellular stress response. Moreover, due to the great increase in sunscreen use in recent years, some of the active components have been detected in increasing concentrations in the environment proving adverse effects. Indeed, significant concentrations of both $TiO_2$ and ZnO have been found in coastal waters.

UV-FILTERS, METHOD OF PRODUCING THE SAME AND THEIR USE IN COMPOSITIONS, IN PARTICULAR SUNSCREENS

CROSS-REFERENCE TO RELATED APPLICATIONS

This application is a U.S. National Stage Application under 35 U.S.C. § 371 of International Patent Application No. PCT/IB2015/055001, filed Jul. 2, 2015 which claims priority to Portugal Application No. 107747, filed Jul. 2, 2014, which are hereby incorporated by reference in their respective entireties.

TECHNICAL FIELD

The present disclosure relates to new UV-filters, method of producing the same and their use in compositions in particular, cosmetic/pharmaceutical or textile compositions, namely sunscreens cream or sunscreens textile article.

BACKGROUND ART

The use of sunscreens as a protective barrier against skin damage and cancer, by absorbing harmful UVA and UVB rays, is becoming an increasingly important issue. Such products are usually based on $TiO_2$ or ZnO.

It is well known and accepted that exposure to ultraviolet (UV) light from the sun can cause extensive damage to the skin, such as erythema and sun burn. Moreover, long term health effects, in particular skin cancer, can also be developed. The UV spectrum is divided into three regions, according to the wavelength of the light: UVC (200-290 nm), UVB (290-320 nm) and UVA (320-400 nm). UVC radiation is mainly blocked by the ozone layer in the upper atmosphere, while UVB and UVA are not; they can, therefore, pose a threat to human health. The UV sunlight at the Earth's surface is approximately 98% UVA and 2% UVB, and while UVB is responsible for the most severe damage to DNA and RNA, UVA has important roles in photoaging and photocarcinogenesis. Both forms of UV light interact with the human body through both direct photochemistry and the formation of secondary radicals and reactive oxygen species.

The use of sunscreens is one of the most common and effective ways to prevent the damage associated to UVA and UVB radiations. Ideally, a sunscreen product should protect the skin in both the UVA and UVB regions to fully prevent the described health problems. Moreover, a sunscreen should be stable over time, and not degrade under irradiation. It is also important that the chemicals the sunscreen is made of are non-toxic for human health, do not cause irritation to the skin, and do not penetrate in the skin itself.

Titanium dioxide ($TiO_2$) and zinc oxide (ZnO) are the most common inorganic materials used in commercial sunscreens: both compounds provide protection over the whole UV range. Literature data show that using these compounds in the form of nanoparticles improves their effectiveness, leading to an enhanced protection. At the same time, however, there is concern about the possible toxicity of the nanoparticles; although several studies were published on the subject, to date there is no incontestable evidence on this topic. For $TiO_2$ and ZnO use, however, another possible risk is associated with their photocatalytic properties under UV and visible light. Both minerals are in fact photochemically reactive compounds; this means that, under irradiation, they can form free radicals and other reactive species that can cause some of the health problems associated with UV exposure. Scientific studies, for instance, showed that the formation of radical species can occur for ZnO-containing sunscreens under illumination, and such reactive species could potentially be as dangerous for the skin as much as the UV light itself. Small $TiO_2$ particles have also been shown to have serious effects on mitochondrial function, altering 85 biochemical metabolites, many of which are associated with the cellular stress response. Moreover, due to the great increase in sunscreen use in recent years, some of the active components have been detected in increasing concentrations in the environment proving adverse effects. Indeed, significant concentrations of both $TiO_2$ and ZnO have been found in coastal waters.

These facts are disclosed in order to illustrate the technical problem addressed by the present disclosure.

General Description

HAp is the main component of bone; it is, therefore, highly biocompatible. In the present disclosure, an iron-doped HAp-based material, containing both Fe ions substituted into the HAp structure and iron oxide in hematite ($\alpha$-$Fe_2O_3$) form, preferably from waste cod fish bones. In an embodiment, this was achieved through a simple process of treating the bones in a Fe (II) containing solution, followed by heating at 700° C. The compound showed good absorption in the whole UV range and did not form radicals when irradiated. Sun cream formulated with this material could be used as a broad sunscreen protector ($\lambda$crit>370 nm), showing high absorption both in the UVA and UVB ranges. Because of its absorption properties it would be classified as 5 star protection according to the Boots UVA star rating system. The cream is also photostable, and does not cause irritation or erythema formation when in contact with human skin. These results show that a food by-product such as fish bones could be converted into a valuable product, with potential in health care and cosmetics. This is the first time a HAp-based sunscreen cream has been developed and the effect of this sunscreen is showed.

Sunscreens are cosmetic compositions that absorb UV radiation.

A HAp-based compound, which comprises Fe, and/or $\alpha$-$Fe_2O_3$ in hematite form and/or $Ca_9FeH(PO_4)_7$, was successfully obtained in particular from fish cod bones; this can be achieved with a simple process of treating the bones, in particular cod fish bones in Fe (II) containing solution and successive bones calcination at 700° C.

The HAp-based compound doped with iron and/or containing $\alpha$-$Fe_2O_3$ in hematite form and/or $Ca_9FeH(PO_4)_7$, showed good absorption properties in the UV range, and it does not form radicals and/or reactive species under irradiation; it was, therefore, used in the formulation of a sunscreen cream.

Tests of a sunscreen composition containing HAp-based compound doped with iron and/or containing $\alpha$-$Fe_2O_3$ in hematite form and/or $Ca_9FeH(PO_4)_7$, in particular in cream containing 1-30% p/v of the said HAp-based compound, namely 15% of the powder revealed that it could be used as a broad sunscreen protector ($\lambda_{crit}$>370 nm), as it shows high absorption both in the UVA and UVB ranges; and its absorption properties it is classified as 5 stars according to Boots UVA protection categories. The cream is also photostable and it does not cause irritation or erythema formation when in contact with human skin.

These results show how a Hap, in particular food by-product such as fish bones Hap could surprisingly be converted into a valuable product as a sunscreen composition, in particular a cream or a water-oil emulsion.

Hydroxyapatite ($Ca_{10}(PO_4)_6(OH)_2$, HAp) is a calcium phosphate compound, highly present in nature. It is a non-toxic material, being the main component of human and animal bones; it has a high biocompatibility; because of this, HAp is used to make bone and dental implants. Because of its non-toxicity, it would be a very suitable material as base for sunscreen filters. Unmodified HAp, however, does not absorb in the UV range, so it is necessary to modify its structure to obtain a UV-absorbing material. Doping with appropriate elements may provide final compounds with promising UV protection.

The majority of HAp used today is synthetic. Several methods have been reported for its preparation, which are normally based on a reaction between calcium- and phosphorus-containing compounds. However, HAp can also be obtained from natural sources in particular from waste by-products with several environmental benefits; namely, HAp-based materials can be extracted from cod fish bones (a waste by-product of the fish industry) as a valorisation product. The results showed that both single-phase HAp, and a bi-phasic material made of HAp and β-tricalcium phosphate (β-TCP), can be obtained by simply calcining the bones.

The present disclosure surprisingly show a HAp-based multiphasic material with UV-absorbing properties and, hence, showing potential use as a sunscreen. The material may be obtained from the cod fish bones using the same principles applied before—that is by modifying them with a suitable treatment in solution. In this case, the bones were treated in a Fe (II) solution and successively calcined; iron was chosen considering the previous published results and because it is, potentially, less toxic than manganese. The product was a multiphasic material containing, HAp, Fe-substituted HAp and a small amount of hematite, and it absorbed radiation over the whole UV range, without releasing any radical species under irradiation. Considering these properties, this sample was tested as an additive in a cream to explore its potential as sunscreen cream. To the best of our knowledge, this is the first time that a HAp-based sunscreen cream has been formulated. The UV protection efficacy and the photostability of the cream were assessed; moreover, a test to determine the dermatological sensitivity to the cream was also performed.

The present disclosure relates to a hydroxyapatite based-compound comprising Fe ions substituted into the HAp structure and/or $\alpha$-$Fe_2O_3$ in hematite form for use in a method for protecting the skin against UV radiation.

This disclosure also relates to a hydroxyapatite based-compound comprising $Ca_9FeH(PO_4)_7$ for use in a method for protecting the skin against UV radiation.

Furthermore, the present disclosure relates to a composition comprising a therapeutically an effective amount of hydroxyapatite compound as described previously and a suitable amount of excipients in the form of a topic formulation.

In an embodiment, the composition comprises said hydroxyapatite compound between 1-30% w/v, preferably between 5-25% w/v, more preferably between 10-20% w/v.

In an embodiment, the composition further comprises an emulsifier, a stabilizer, a thickener, dyes, fragrances, and/or a preservative.

In an embodiment, the composition comprises at least one emulsifier selected from the following list: TEGO® CARE 450 (polyglyceryl-3 methylglucose distearate), stearic acid.

In an embodiment, the composition comprises xantham gum as a thickener.

In an embodiment, the composition further comprises glycerine.

In an embodiment, the composition is in the form of a cream, in the form of a water-oil emulsion.

The present disclosure relates also to the use of hydroxyapatite compound comprising $\alpha$-$Fe_2O_3$ in hematite form as a UVA and/or a UVB sunscreen agent, in particular $Ca_9FeH(PO_4)_7$.

Throughout the description and claims the word "comprise" and variations of the word, are not intended to exclude other technical features, additives, components, or steps. Additional objectives, advantages and features of the solution will become apparent to those skilled in the art upon examination of the description or may be learned by practice of the solution.

BRIEF DESCRIPTION OF THE DRAWINGS

The following figures provide preferred embodiments for illustrating the description and should not be seen as limiting the scope of present disclosure.

FIG. 4: (a) UV spectrum of the sample Fe-HAp in absorbance mode. (b) Normalised absorption for samples Fe-HAp, commercial $TiO_2$ P25 and commercial ZnO Merck.

FIG. 5: Absorbance of ABTS radical under (a) UV and (b) white light irradiation. Schematic representation of a preferred embodiment where:
(1) CD stands for control sample in the dark,
(2) CL stands for ABTS solution under light irradiation without any powder
(3) Fe.HAp, $TiO_2$ and ZnO stands for ABTS under light irradiation in contact with powder samples Fe-Hap, commercial $TiO_2$ P25 and commercial ZnO Merck respectively.
(4) Column with the same symbol (*,  or *) indicate that data are NOT statistically different.

FIG. 7: UV spectra for the cream samples; (a-b) spectra of the creams as prepared; (c-d) spectra of the creams after light irradiation; (a-c) creams prepared with hot emulsion; (b-d) creams prepared with cold emulsion.

DETAILED DESCRIPTION

In the present disclosure, an iron-doped HAp-based (Hydroxyapatite) compound, containing both Fe ions substituted into the HAp structure and iron oxide in hematite ($\alpha$-$Fe_2O_3$) form, showed good absorption in the whole UV range and did not form radicals when irradiated. Because of its absorption properties it would be classified as 5 star protection according to the Boots UVA star rating system. The cream is also photostable, and does not cause irritation or erythema formation when in contact with human skin.

In an embodiment, the powder was prepared, in particular cod fish bones were washed and stored at −20° C. Prior to use, they were defrosted and dried at 45° C. overnight.

To prepare the samples, a weighed amount of bones was placed in an iron (II) chloride ($FeCl_2$) solution. $FeCl_2$ concentration was 5 times higher than the HAp concentration, calculated assuming a 70% HAp content in the fish bones. The pH of the solution, initially acidic (2.9-3), was adjusted to 8.0 with the addition of 1M $NH_4OH$ solution.

The bones were left stirring in this solution for 3 hours, at 65-70° C. The bones were then dried at 45° C. overnight, and then calcined at 700° C.; the heating/cooling rate was 5° C./min, while the calcining time was 1 hour.

In an embodiment, the powder characterisation was performed. To establish the elemental composition of the sample, the concentration of calcium, phosphorus and iron were measured. A weighed amount of sample was dissolved in a $HNO_3$ solution, which was then used to determine the concentration of each element. For calcium, flame atomic absorption spectroscopy (FA-AAS) was used, with a UNI-CAM 960® spectrophotometer (Waltham, USA). Phosphorus was determined by a spectrophotometric method: the solution was reacted with the Merck Spectroquant phosphorus reagent kit, containing an acidified solution of $NH_4VO_3$ and $(NH_4)_6Mo_7O_{24} \cdot 4H_2O$ to form an orange-yellow coloured compound of $H_4PMo_{11}VO_{40}$ (molybdovanadophosphoric acid). This compound was analysed spectrophotometrically, using a Perkin Elmer Lambda 25 spectrometer, at 400 nm, against a calibration curve of $KH_2PO_4$ standard solutions.

In an embodiment, the total iron concentration was determined by an Inductively Coupled Plasma (ICP) optical emission spectrometer (Optima 7000 DV, Perkin Elmer, USA) with radial configuration. The concentration of Fe (III), on the other hand, was determined with a spectrophotometric method, by measuring the absorbance of the complex formed between the Fe (III) and thiocyanate SCN— ions at 447 nm (C. R. Clark, J. Chem. Educ., 1997, 74, 1214), against a calibration curve of Fe (III) standard solutions. Fe (II) concentration was determined by subtracting the Fe (III) concentration from the total iron concentration.

In an embodiment, the phase composition of the samples was determined using X-ray diffraction (XRD). Semi-quantitative phase analysis (QPA), which estimates the relative amounts of crystalline phases in the samples without accounting for any amorphous phase present, was made using the Rietveld method. XRD data for QPA were collected using a θ/θ diffractometer (PANalytical X'Pert Pro, NL) equipped with a fast RTMS detector (PANalytical PIXcel-1D) with Cu Kα radiation (40 kV and 40 mA, 20-80°2θ range, a virtual step scan of 0.02°2θ, and virtual time per step of 50 s). Instrumental contribution, obtained from the NIST SRM 660b standard ($LaB_6$), was also taken into account in the refinement. The starting atomic parameters for HAp, $Ca_9FeH(PO_4)_7$ and $\alpha$-$Fe_2O_3$ were taken from the literature. The Rietveld data analysis was then performed using the GSAS software package, taking advantage of its graphical interface EXPGUI (A. C. Larson, R. B. Von Dreele, General Structure Analysis System (GSAS). Los Alamos National Laboratory Report LAUR, 2004, and B. H. Toby, J. Appl. Cryst., 2001, 34, 210). The following parameters were refined: scale-factors, zero-point, six coefficients of the shifted Chebyshev function to fit the background, unit cell parameters, and two Lorentzian ($L_X$ and $L_Y$) terms for profile coefficients.

In an embodiment, FT-IR spectroscopy was performed with a Perkin Elmer Spectrum 100. To acquire the spectra, about 5 mg of sample was mixed with 200 mg of KBr; the homogeneous mixture was then pressed into a pellet. Spectra were acquired in transmittance mode.

In an embodiment, the sample surface morphology was analysed with Scanning Electron Microscopy (SEM), using a Hitachi S-4100 at 25 kV. Because of its insulating properties, the powder was pressed into discs and then sputtered with a gold/platinum coating before the analysis.

In an embodiment, the UV-vis spectra were taken using a Shimadzu UV 3100 spectrometer equipped with an integrating sphere, covering a wavelength range between 250 and 850 nm (0.2 nm step-size, $BaSO_4$ as reference). UV-vis spectra were taken of the fish bone derived powder, as well as for commercial samples of $TiO_2$ and ZnO (P25 Degussa and Merck, respectively).

In an embodiment, to test the photoactivity of the powder, a test with 2,2'-azino-bis-3-ethylbenzthiazoline-6sulphonic acid (ABTS) was used. ABTS was dissolved in water and appropriately diluted to have an absorbance value of about 0.720 for λ=734 nm. A powder sample solution, with a concentration of 1.0 mg/ml, was prepared; appropriate aliquots of the solution were added to the ABTS solution in a closed 5 cm petri dish; the final concentration of the powder was 0.125 mg/ml, while the total volume was 5 ml. The dishes were then irradiated with both UV and white light. For the UV irradiation, a XX-15 BLB UVP lamp was used ($\lambda_{max}$=365 nm), with an irradiation density of 0.80 mW cm. For the white light, a Philips TLD 58W/84 fluorescent lamp, with spectral emission of 400 nm<λ<700 nm was employed. In both cases, the irradiation time was 15 minutes.

At the end of the irradiation, samples were centrifuged at 7000 rpm for 10 minutes, to separate the powder from the solution. The absorbance of the supernatant was then measured at λ=734 nm.

In an embodiment, the test was performed for the powder derived from fish bones, as well as for commercial $TiO_2$ and ZnO powders (see above). Control experiments were performed with samples kept in the dark for the same interval of time.

In an embodiment, the cream used to incorporate the powder was an emulsion made of two phases, one aqueous and one oily. The oily phase was made of TEGO® CARE 450 (polyglyceryl-3 methylglucose distearate) with capric, stearic and cetylic acids, in concentrations of 3, 4, 2 and 3 w/w respectively; the water phase, on the other hand, was made of glycerine and xantham gum in concentrations of 2 and 0.6 w/w. The final weight was then adjusted to 100 g with the addition of distilled water. The two phases were prepared separately, heated at 80-90° C. and then mixed when they were still warm.

In an embodiment, the powder was added to the emulsion in different concentrations—between 1 and 20%. Two sets of experiments were carried out: in the first the powder was added when the emulsion was still hot, while in the second the powder was added when the emulsion had been cooled down to room temperature. These two kinds of experiments correspond to the emulsions H and C respectively. As a reference (R), a cream with no additive, was also prepared. For both sets of experiments, the emulsion was stirred using a R17 Marienfeld mechanical stirrer while the powder was added. The stirring rate was different depending on the amount of powder added; in all cases, however, care was taken to ensure a homogeneous distribution of the powder in the emulsion.

In an embodiment, the colour of the creams was measured using a Konica Minolta Spectrometer CM-700d); the instrument was calibrated with a standard white plate, with coordinates L=97.59, a*=0.07, b*=1.89. Data were expressed using the CIELab system. For each cream, the difference in colour was evaluated with the formula:

$$\Delta E=[(L_{sample}-L_{reference})^2+(a^*_{sample}-a^*_{reference})^2+(b^*_{sample}-b^*_{reference})^2]^{0.5}$$

where the reference is the cream without the addition of any powder (R).

Statistical analysis (Anova test) was performed to compare the colour data, with a 95% probability (P<0.05).

In an embodiment, the in vitro determination of UV protection was conducted. The photo-protection efficiency of the creams was determined by measuring the UV-Vis absorption spectra, with the same spectrometer used for the powder sample (see above). For the measurements, a weighed amount of cream was uniformly spread on the base of a polystyrene petri dish, forming a 2 mm thick layer. Prior to the testing, the cream was dried at 45° C. for 1 hour. Two measurements were taken for each sample. The UV-Vis spectrum of the polystyrene plate was also acquired, and subtracted from the spectra of each cream sample.

The effectiveness of the UV protection was evaluated by the critical wavelength method (Colipa, In vitro method for the determination of the UVA protection factor and "critical wavelength" values of sunscreen products. Revised Guidelines (2011).), where the value of the critical wavelength was calculated with the formula:

$$\int_{290}^{\lambda crit} A_\lambda d\lambda = 0.9 * \int_{290}^{400} A_\lambda d\lambda$$

Moreover, the UVA/UVB ratio was also calculated (M. V. R. Velasco, F. D. Sarruf, I. M. N. Salgado-Santos, C. A. Haroutionian-Filho, T. M. Kaneko, A. R. Baby, Int. J. Pharmac., 2008, 363, 50), according to the formula:

$$R = \frac{\int_{320}^{400} \frac{A_\lambda d\lambda}{\int_{320}^{400} d\lambda}}{\int_{290}^{320} \frac{A_\lambda d\lambda}{\int_{290}^{320} d\lambda}}$$

In an embodiment, to establish the stability of the creams, and their efficacy as photoprotectors, all samples were irradiated with both UV and white light, using the same light sources described above. The irradiation times were 3 and 1 hour for UV and white light respectively. After the irradiation, the UV-Vis spectra of all samples were acquired again.

The stability was assessed with the Area Under the Curve Index (AUCI); according to literature (D. Garoli, M. G. Pelizzo, B. Bernardini, P. Nicolosi, M. Alaibac, J. Dermat. Sci., 2008, 52, 193.) the AUCI parameter is calculated considering the area under the curve (AUC) of the UV absorption spectrum in the interval 290-400 nm. This area is calculated before and after the irradiation, with the AUCI being: AUCI=(AUC) after/(AUC) before. If the AUCI is higher than 0.8, the sunscreen is considered stable. The same calculation was done considering the intervals 320-400 and 290-320 nm to determine the specific stability in the UVA and UVB regions (AUCIA and AUCIB, respectively).

In an embodiment, to assess the safety of the developed cosmetic product, its acute irritant potential was tested in human volunteers after a single application under occlusion (patch test). The effect of the selected samples of cream on human skin was tested according to Colipa protocol (Colipa, Assessment of skin tolerance of potentially irritant cosmetic ingredients. Guidelines (2007) on 20 healthy volunteers; their group age was 20-50, subjects with previous problems of skin sensitivity and skin allergic reactions were excluded. Finn Chambers on Scanpor (8 mm diameter, SmartPractice®) were used to put the cream in contact with the skin. About half of the volume of each chamber was carefully filled with the cream; then a patch was applied to the forearm of the volunteer. As a negative control, the cream without any additive (R) was also used. After 48 hours, the patches were removed and the reaction of the skin was evaluated 30 minutes after the patch removal, following the ESCD guidelines. The guidelines are based on a scoring scale from 0 to 4, where 0 corresponds to no skin reaction/irritation while 4 indicates a very strong reaction (R. A. Tupker, C. Willis, E. Berardesca, C. H. Lee, M. Fartasch, T. Agner, J. Serup, Cont. Derm., 1997, 37, 53.). This study was performed following the WMA Declaration of Helsinki and the Informed Consent protocol.

Materials Characterisation

Figure 1:
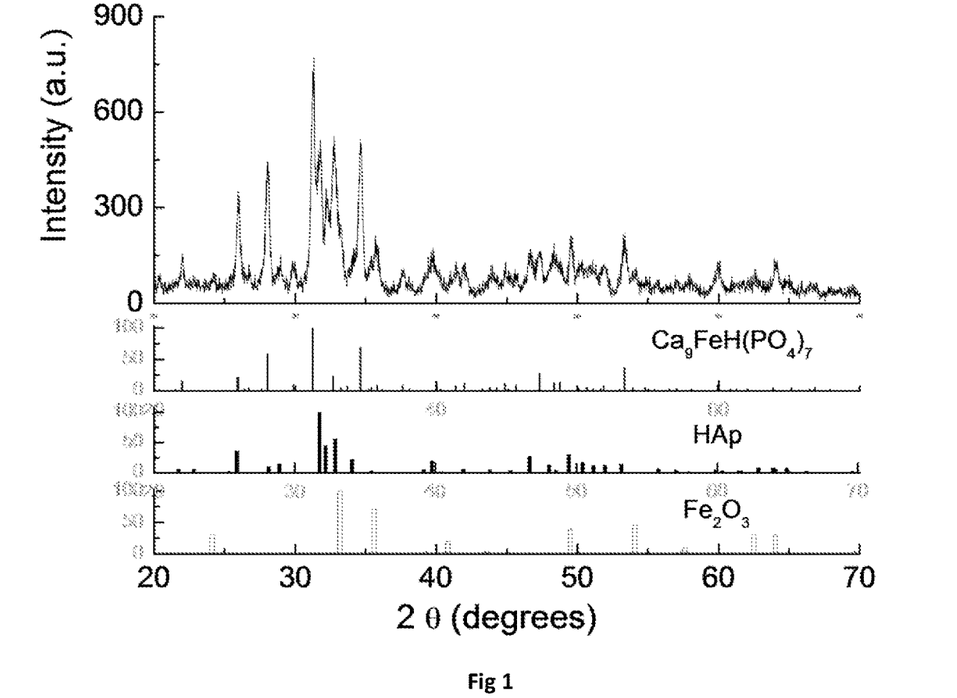
FIG. 1: XRD pattern for sample Fe-Hap.

FIG. 1 shows the XRD diffraction pattern for the powder obtained after Fe (II) solution treatment and calcination of the fish bones (sample HAp-Fe); the corresponding phase composition is reported Table 1. It can be seen that, although HAp is still present, it is not the main phase anymore, as its concentration is about 43 wt %. The main component is a different phosphate-based compound, which contains both iron and calcium—$Ca_9FeH(PO_4)_7$ (calcium hydrogen iron phosphate), with about 55 wt % concentration. Further to this, a small amount of 2 wt % hematite was also detected, at the limits of XRD sensitivity—the actual amount may well be less than 2 wt %. The detection of these phases indicates that iron is present with two different oxidation states, both as Fe (II) and Fe (III), in the mixed phosphate and hematite, respectively.

TABLE 1

Phase and elemental composition of HAp-Fe sample; all values are expressed as weight %. For the phase analysis, Rietveld agreement factors were: $R_{wp}$ = 5.90%, $R(_F^2)$ = 6.04%, $\chi^2$ = 1.63.

| Phase | Concentration |
|---|---|
| $Ca_{10}(PO_4)_6(OH)_2$ | 42.9(3) |
| $\alpha$-$Fe_2O_3$ | 2.0(2) |
| $Ca_9FeH(PO_4)_7$ | 55.0(3) |
| Element | |
| Ca | 31.64 |
| P | 18.59 |
| Fe total | 3.90 |
| Fe (III) | 1.04 |
| Fe (II) | 2.86 |

To explain this, the chemical reactions taking place in solution and during the calcination have to be considered. In solution, the addition of a base led to the formation of Fe (II) oxide, which formed a suspension; the colour change of the solution from green to dark brown/black confirmed this. When the bones were treated in solution, some of the Fe (II) was substituted into the HAp lattice, due to an ion exchange process. Indeed, it is well known that the HAp lattice structure favours the exchange between Ca (II) and other divalent ions. Moreover, in this case the ion exchange is also favoured by the porous structure of the bones themselves. During the calcination, Fe-containing HAp was partially converted into Fe-containing phosphate, leading to the formation of $Ca_9FeH(PO_4)_7$; this process was previously reported in literature for HAp samples with iron embedded into their lattice. A. Tampieri, T. D'Alessandro, M. Sandri, S. Sprio, E. Landi, L. Bertinetti, S. Panseri, G. Pepponi, J. Geottlicher, M. Bañobre-López, J. Rivas, Acta Biomat., 2012, 8, 843.

Further to the ion exchange, however, the Fe (II) oxide suspension also formed a layer on the surface of the bones; this could be observed, as at the end of the treatment the bones had a darker colour. During the calcination, an oxidation of this iron oxide took place, due to the reaction of Fe (II) with atmospheric oxygen, resulting in the formation of Fe (III) oxide in the form of hematite.

Table 1 also shows the elemental analysis of the powder. The data confirm the presence of iron in both forms; in fact it can be seen that the total iron concentration is higher than the Fe (III) concentration alone (Fe(III) ~27% of total Fe), indicating the presence of Fe (II) as well. These data are in agreement, within the experimental error, with the phase composition values calculated by XRD semi-quantitative phase analysis.

Figure 2:
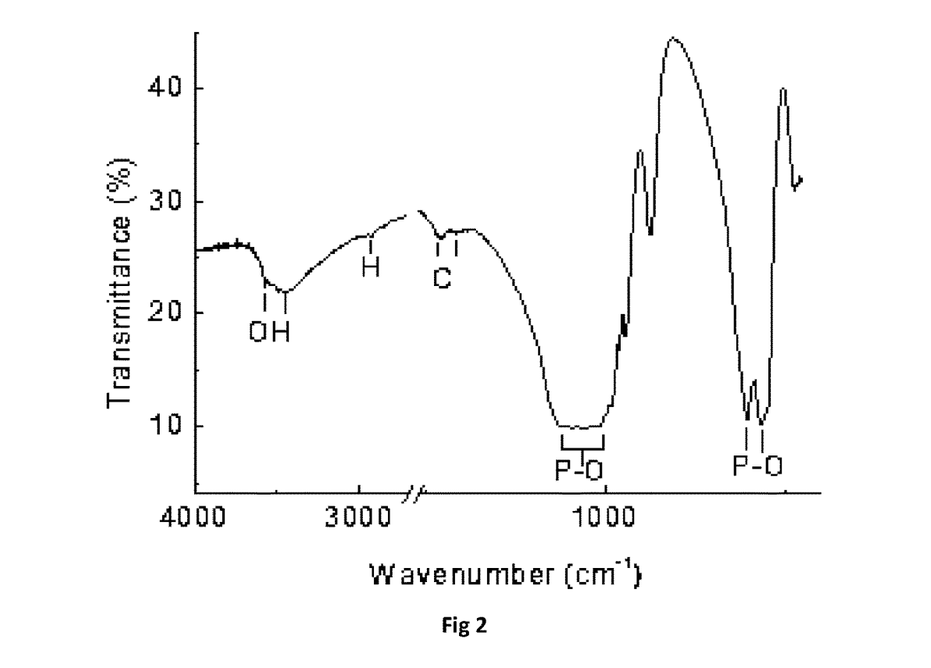
FIG. 2: Infrared spectrum of the sample Fe-Hap.

In FIG. 2, the IR spectrum of sample HAp-Fe based compound is reported. The P—O related peaks can be observed in wavelength intervals of 540-620 $cm^{-1}$ and 900-1200 $cm^{-1}$. Considering this last region in particular, it can be seen that the spectrum just shows one broad peak, and not several sharp ones as is normally observed for HAp. This behaviour was previously reported for $Ca_9FeH(PO_4)_7$; it therefore confirms the presence of this phase in the material. The small peak detected at 2925 $cm^{-1}$ also belongs to $Ca_9FeH(PO_4)_7$, as it is due to the proton present in this molecule (23. M. Dondi, F. Matteucci, G. Cruciani, G. Gasparotto, D. M. Tobaldi, Solid State Sci, 2007, 9 362).

The spectrum also has signals in the 1410-1460 $cm^{-1}$ region, which correspond to carbonate ions; their presence is due to the fact that organic fragments may still be present in the powder. In fact, literature reports that a complete elimination of the organic fraction from the bones can take place only for temperatures as high as 1000° C. The broad signal at 3450 $cm^{-1}$, together with the small sharp peak at 3570 $cm^{-1}$, is due to the OH group of the HAp molecule.

Figure 3:
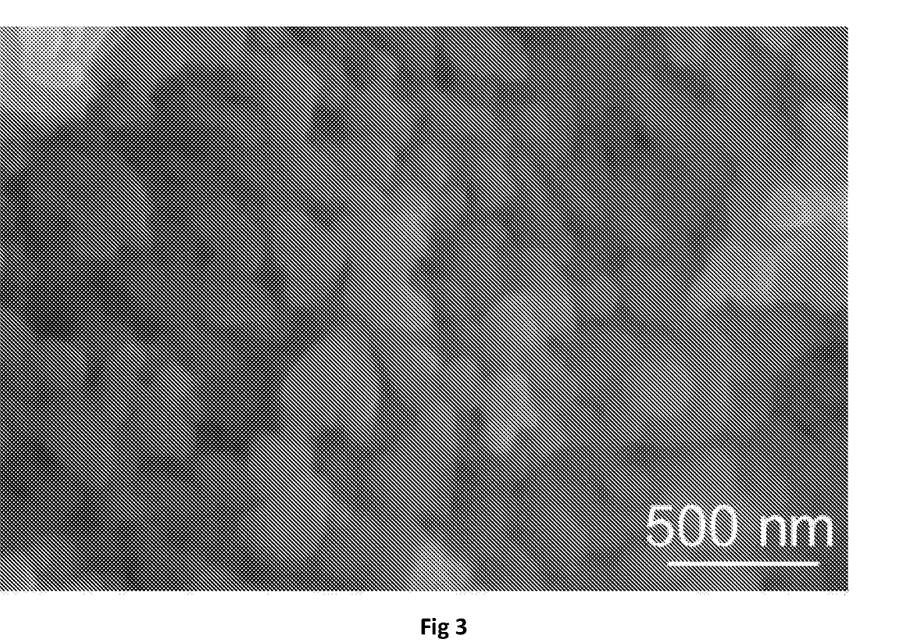
FIG. 3: SEM micrography for sample Fe-HAp, 50 000 magnifications.

FIG. 3 shows the SEM micrography of HAp-Fe powder. It can be seen that the material consists of small, submicron, irregularly-shaped grains, with diameters between ~50-200 nm. Most of the particles appear to be around 100 nm, making this a borderline nanomaterial, and they appear to be poorly crystalline in nature, reflecting the relatively broad and noisy XRD pattern obtained. This is reasonable considering the relatively low calcination temperature (700° C.).

Figure 4A:
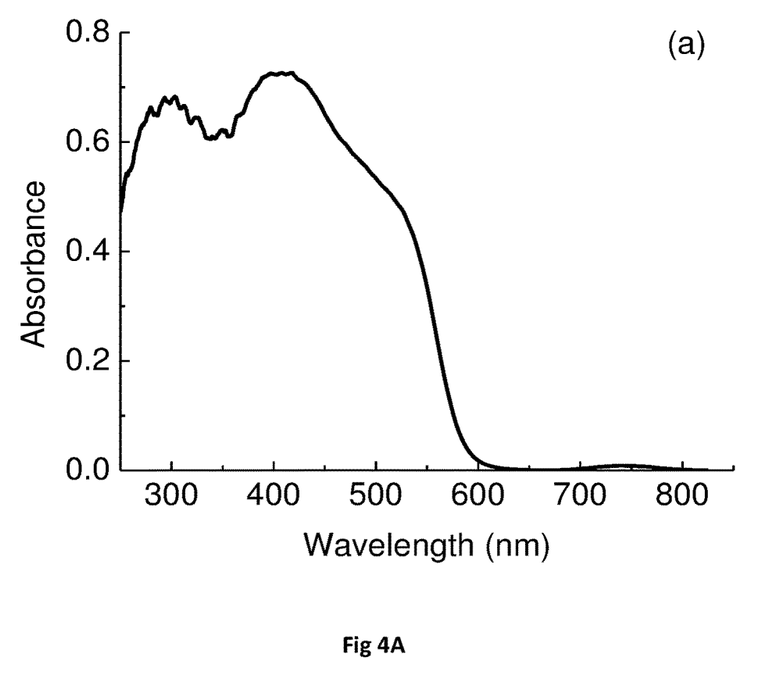

FIG. 4(a) reports the UV-Vis spectrum of HAp-Fe, shown in absorbance mode; the sample absorbs both in the UVA and UVB regions, showing great potential as a sunscreen. In the spectrum, two broad peaks can be observed, centred at about 300 and 408 nm respectively; a shoulder at about 526 nm is also present.

The characteristics observed in the spectra are in agreement with literature data for $\alpha\text{-}Fe_2O_3$, as in the Fe (III) oxide spectrum the most intense UV absorption bands correspond to 290 and 395 nm. They are described to the metal-ligand charge transfer (MLCT), and to a certain extent, also to contribution of $Fe^{3+}$ ligand field transitions: $^6A_1 \rightarrow {}^4T_1(^4P)$ at 290-310 nm, and $^6A_1 \rightarrow {}^4E(^4D)$ and $^6A_1 \rightarrow {}^4T_2(^4D)$ at 360-400 nm. The exact position of these bands, however, can vary due to the characteristics of the powder; in the case of nanoparticles, for instance, the diameter of the particle can affect the light absorption. A similar effect was observed for nanorods, where the values of both diameter and length of the rods influenced the position of the absorption maximum and the intensity of the absorption. Analogously, the absorption in the visible region, and hence the colour of the powder, can also depend on the crystallite size.

Figure 4B:
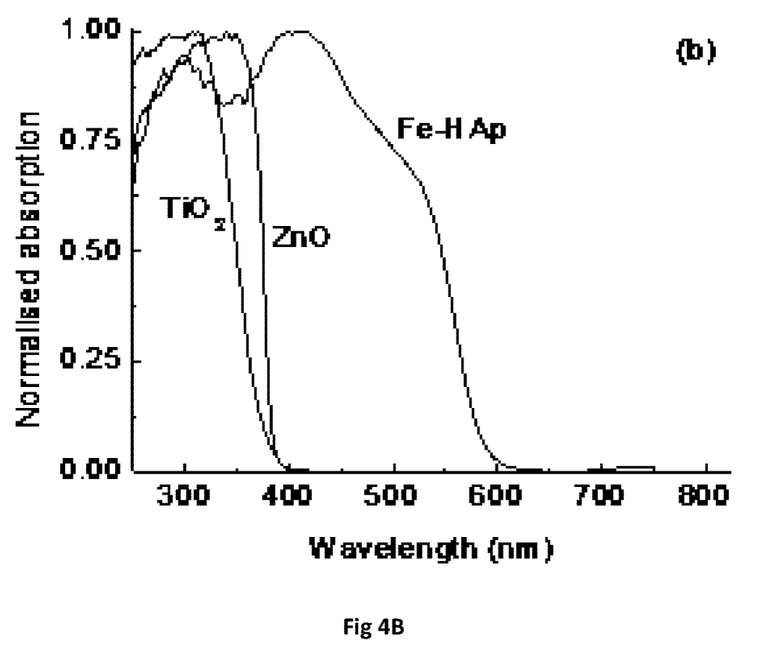

FIG. 4(b) shows the normalised absorption of samples Fe-HAp and commercial $TiO_2$ and ZnO powders; these measurements were performed to compare the UV absorption range of Fe-HAp to that of powders already used for sunscreens. It can be seen that Fe-HAp absorbs for the whole UV range, whereas both commercial samples do not show this feature; in fact their absorption starts to decrease at about 315 and 350 nm for $TiO_2$ and ZnO, respectively. The larger UV absorption range shows that, potentially, Fe-HAp could be a sunscreen with better performance in the UVA interval than some of the commercial samples.

In an embodiment, to test the potential of Fe-Hap sample as an inert sunscreen material, its photoactivity was tested under both UV and white light. A protocol similar to that reported in literature was used (L. Tiano, T. Armeni, E. Venditti, G. Barucca, L. Mincarelli, E. Damiani, Free Rad. Biol. Medic., 2010, 49, 408). The powder was irradiated and, to see if any radical/reactive species were formed, the subsequent reaction with a radical such as ABTS was measured. ABTS was chosen as reagent due to its greater sensitivity if compared with other reagents such as DPPH; moreover, it was previously used to monitor the photoactivity of materials such as $TiO_2$ (V. Brezová, Z. Vrecková, P. Billick, M. Čaplovičová, G. Plesch, J. Photoch. Photobiol. λ2009, 206, 177.) The extent of the reaction was monitored by measuring the absorbance at λ=734 nm. With no radical formation, no reaction should take place and, hence, no change in colour should be observed; the formation of radicals, on the other hand, should lead to a color change in the ABTS solution.

Figure 5A:
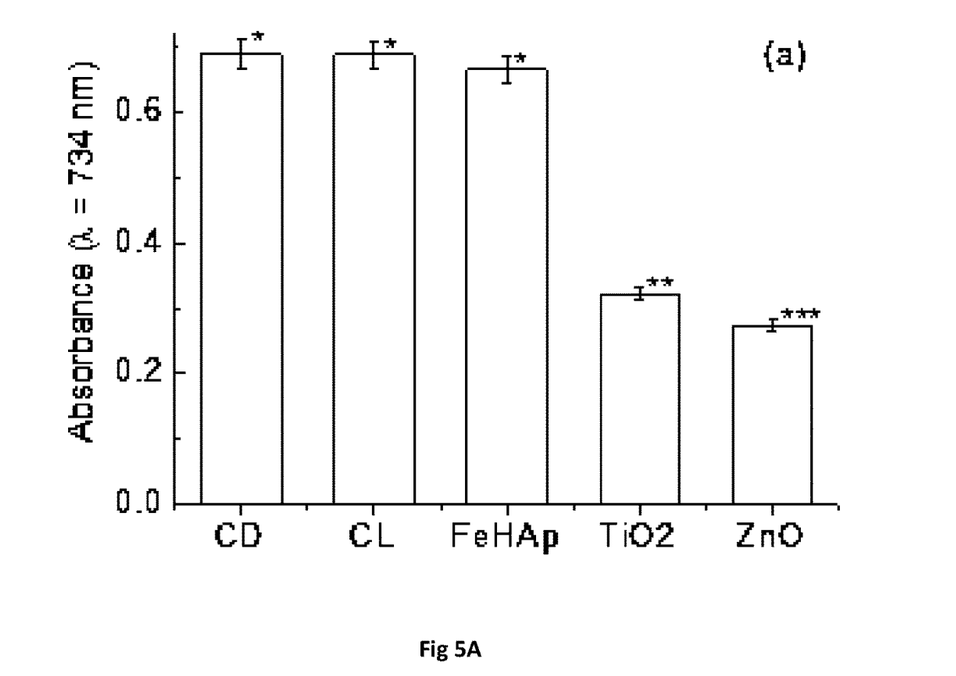
Figure 5B:
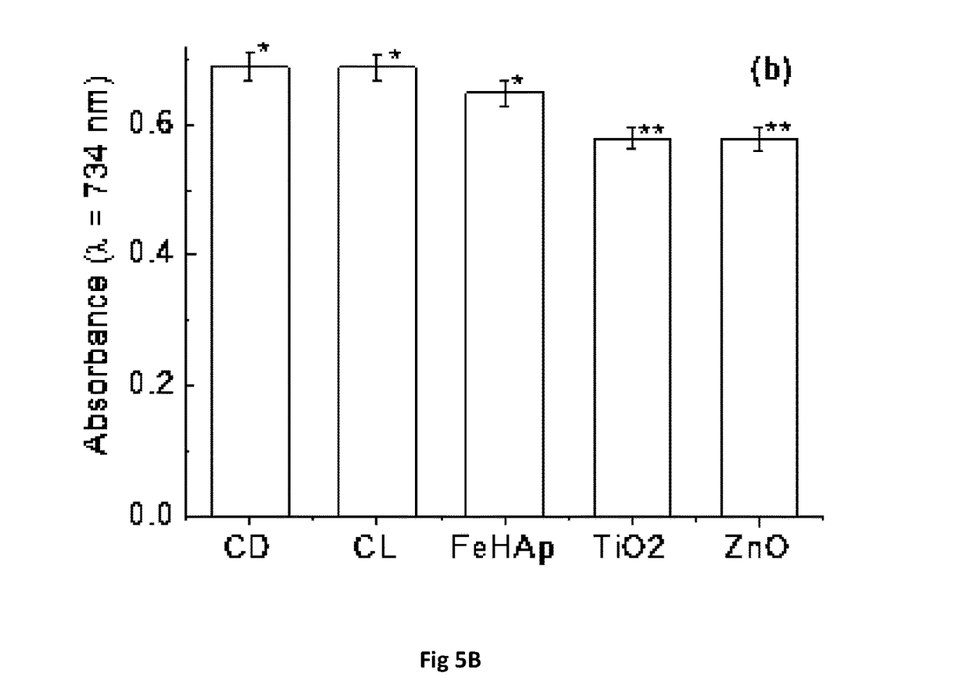

For comparison purposes, the test was also performed for commercial $TiO_2$ and ZnO; the results are shown in FIGS. 5(a) and 5(b) for UV and white light irradiation, respectively. It can be seen that, under UV light, there is no change in the ABTS absorption for Fe-HAp containing solution; for $TiO_2$ and ZnO, on the other hand, a clear decrease can be seen. Under white light, there is a slight decrease in the absorption value; the difference, however, is not statistically significant (P<0.05). In any case, the change observed is smaller than that registered for both $TiO_2$ and ZnO. These data indicate that Fe-HAp is less photoreactive than other inorganic materials used as sunscreen filters; hence, it potentially represents a safer option for a cream formulation.

Testing of the Cream: UV Protection and Photostability

In other embodiment, Table 2 reports the composition of the emulsions prepared adding the HAp-Fe powder to the basic emulsion (see "Cream preparation" section). It can be seen that different powder quantities were added, to see how the additive concentration could affect the absorbing properties of the cream. A maximum HAp-Fe content of 20 wt % was used.

TABLE 2

Emulsions prepared adding different amounts of HAp-Fe sample. The letters H and C indicates that the powder was added to the hot or cold emulsions respectively.

| Sample name | Powder concentration (% w/w) |
| --- | --- |
| R | 0 |
| H-01 | 1 |
| H-05 | 5 |
| H-10 | 10 |

TABLE 2-continued

Emulsions prepared adding different amounts of HAp-Fe sample. The letters H and C indicates that the powder was added to the hot or cold emulsions respectively.

| Sample name | Powder concentration (% w/w) |
|---|---|
| H-15 | 15 |
| H-20 | 20 |
| C-01 | 1 |
| C-05 | 5 |
| C-10 | 10 |
| C-15 | 15 |
| C-20 | 20 |

TABLE 3

CIELab coordinates for the cream samples.

| Sample | L | a* | b* | $\Delta E$ |
|---|---|---|---|---|
| R | 55.32 ± 0.56 [a] | −0.40 ± 0.03 [a] | 1.47 ± 1.19 [a] | — |
| H-01 | 30.21 ± 0.72 [b] | 11.18 ± 0.43 [b] | 10.70 ± 0.17 [b] | 29.15 ± 0.65 [a] |
| H-05 | 27.25 ± 0.91 [c] | 10.30 ± 0.46 [b] | 8.08 ± 0.20 [c] | 30.76 ± 0.79 [a] |
| H-10 | 24.29 ± 0.83 [d] | 10.67 ± 0.08 [b] | 7.33 ± 0.37 [d] | 33.46 ± 0.59 [b] |
| H-15 | 23.51 ± 0.17 [d] | 11.28 ± 0.31 [b] | 6.99 ± 0.19 [d] | 34.33 ± 0.64 [b] |
| H-20 | 23.98 ± 0.43 [d] | 10.15 ± 0.31 [b] | 6.18 ± 0.16 [e] | 33.40 ± 0.62 [b] |
| C-01 | 39.43 ± 0.73 [e] | 5.62 ± 0.54 [c] | 8.09 ± 0.36 [c] | 18.23 ± 0.84 [c] |
| C-05 | 27.79 ± 0.58 [c] | 9.85 ± 0.37 [b] | 8.17 ± 0.60 [c] | 30.13 ± 0.77 [a] |
| C-10 | 25.75 ± 0.36 [f] | 11.13 ± 0.05 [b] | 7.60 ± 0.11 [d] | 32.32 ± 0.61 [b] |
| C-15 | 25.16 ± 0.26 [f] | 11.21 ± 0.24 [b] | 7.42 ± 0.19 [d] | 32.86 ± 0.63 [b] |
| C-20 | 27.44 ± 0.15 [c] | 10.12 ± 0.29 [b] | 7.13 ± 0.17 [d] | 30.33 ± 0.69 [a] |

Note:
different letters in the same column indicate that data are statistically different (P < 0.05).

Figure 6:
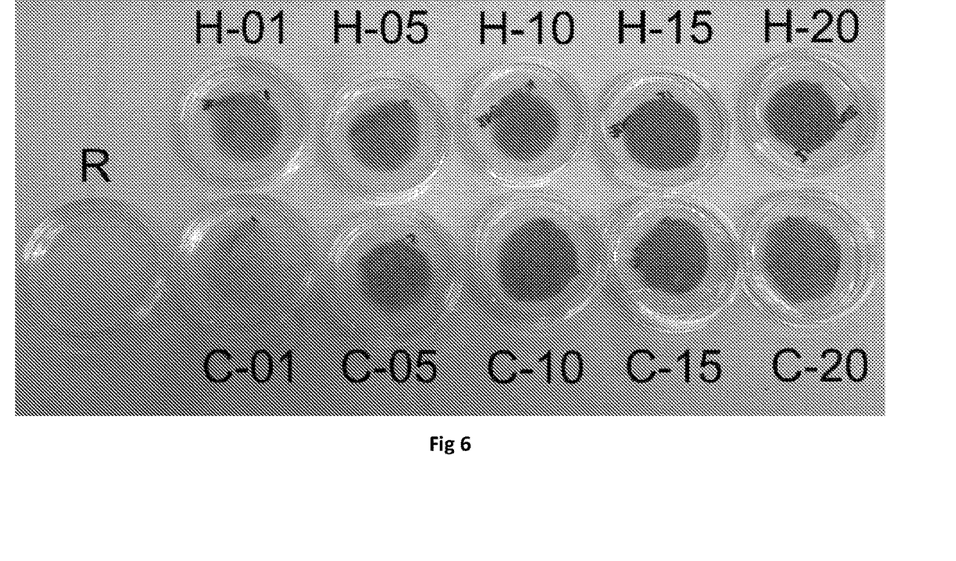
FIG. 6: Picture of the creams prepared, as detailed in Table 2.

FIG. 6 shows a picture of all the creams with different powder concentrations, as well as the reference cream. It can be seen how the cream colour changes depending on the additive content and the preparation method. The pictures show that all creams have a colour which is similar to other cosmetic products, and for that, acceptable for the consumer.

To evaluate quantitatively the colour of each cream, the CIELab coordinate system was used; the results for each cream are listed in Table 3, together with the total difference in colour $\Delta E$. A statistical analysis was also performed to compare the same parameter (CIELab coordinate or $\Delta E$) for different creams (i.e. a comparison of the different data in the same table column).

In the creams prepared at high temperature (samples H), a decrease in the luminosity parameter L is observed in comparison to the reference cream R; such decrease is more marked for the creams with higher HAp-Fe powder concentrations. Both a* and b* values, on the other hand, are higher than for the unmodified emulsion R, indicating a colour shift towards the red and the yellow respectively. For the a* parameter, however, there is no statistical difference between the various samples, while for b* a significant (P<0.05) decrease with increasing additive concentration can be observed. Those prepared in cold conditions (samples C) also present a decrease in the L value, but they exhibit a clear general increase in a*, along with a much smaller general decrease in b*, with increasing HAp-Fe content. Apart from sample C01, all cream samples with HAp-Fe powder added exhibited similar colour change ($\Delta E$) values of 29-34. Considering the difference in $\Delta E$ between creams prepared under hot and cold conditions, samples with 5, 10 and 15 wt % additive contents showed comparable $\Delta E$ values (values not statistically different, P>0.05), regardless of the preparation conditions. The creams with 1 and 20 wt % additive concentrations, however, did not follow this pattern; in fact those prepared in cold conditions (C01 and C20) had lower $\Delta E$ values than those prepared warm (H01 and H20). This may be because in the creams prepared at higher temperatures, a more homogenous mixture between the powder and the emulsion was obtained; the effect that the powder has on the colour is, therefore, more enhanced.

Figure 7A:
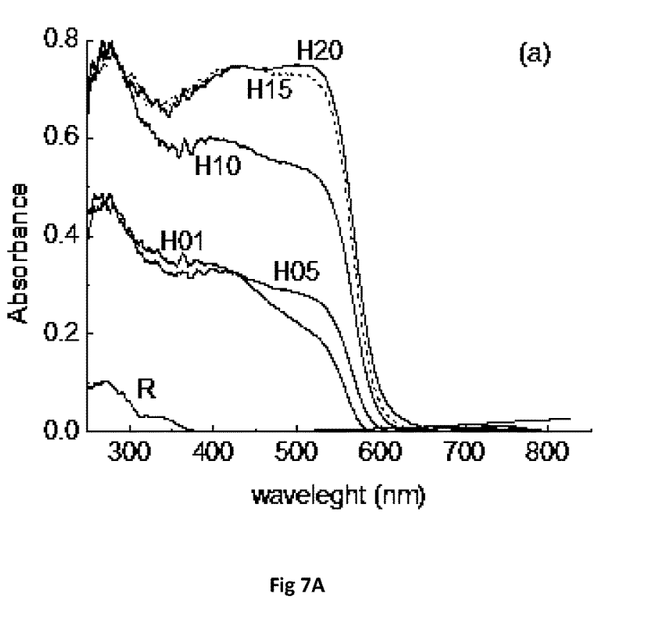
Figure 7B:
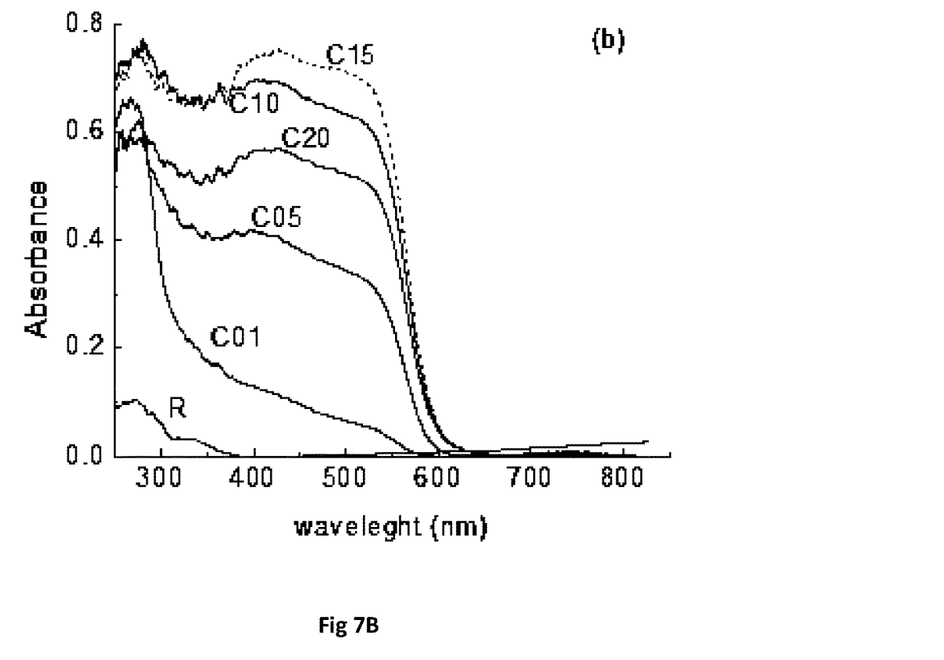

The UV-Vis spectra of the creams prepared in hot and cold conditions are shown in FIGS. 7(a) and 7(b) respectively; the spectrum of the unmodified cream (R) is also shown in both graphs. It can be seen that R shows very little absorption in the UV and almost none in the visible; this later was predictable from its white colour (see FIG. 6 and Table 3). Considering FIG. 7(a), it can be seen that the absorption spectrum of all creams maintained the same profile of the powder, as shown in FIG. 4(a), with absorption over the whole UV range. Spectra of samples H01 and H05 show almost no difference; a further increase in the additive concentration led to an increase in the value of the absorption, as can be seen for samples H10 and H15. A HAp-Fe content higher than 15%, however, did not cause any further increase in the UV absorption; in fact the spectra of sample H15 and $H_2O$ are practically identical (within experimental error).

The samples prepared at room temperature, on the other hand, show different characteristics. Sample C01, in particular, shows high absorption only for wavelengths smaller than 300 nm; for higher values a sudden decrease can be observed. Creams with higher additive content have a similar absorption profile to the HAp-Fe powder; it is interesting to note, however, that sample C20 has a lower absorption than C10 and C15. Both these anomalies could be due to an incomplete homogenisation and distribution of the additive in the cream paste due to the lower temperature. For C01, it is possible that, as the powder was not well distributed and in lower concentration, its contribution to the absorption could have been smaller. For sample C20, on the other hand, HAp-Fe content may have been too high in the cream to embed itself into the structure of the cream properly with the mixing performed at room temperature. The subsequent lack of homogenisation may have had a significant effect on the UV-Vis properties.

To evaluate the effectiveness of the protective action, the critical wavelength $\lambda_{crit}$ and the UVA/UVB ratio were calculated; they are shown in Table 4. It can be seen that the majority of samples have a $\lambda_{crit}$ value between 388 and 390 nm; the only exception is C01, with a value of 382 nm, as its absorption in the UVA range is lower due to the reasons aforementioned. However, all $\lambda_{crit}$ values are higher than 370 nm; therefore, all creams can all be classified as broad spectrum sunscreen.[27] These $\lambda_{crit}$ values are comparable with those of other commercially available inorganic sunscreens.

TABLE 4

Critical wavelength $\lambda_{crit}$ and UVA/UVB ratio for the cream samples.

| Sample | $\lambda_{crit}$ (nm) | UVA/UVB ratio |
|---|---|---|
| H-01 | 388-389 | 0.983 |
| H-05 | 388-389 | 0.942 |
| H-10 | 388-389 | 0.920 |
| H-15 | 389-390 | 1.029 |
| H-20 | 389-390 | 1.025 |
| C-01 | 382-383 | 0.570 |
| C-05 | 388-389 | 0.938 |

TABLE 4-continued

Critical wavelength $\lambda_{crit}$ and UVA/UVB ratio for the cream samples.

| Sample | $\lambda_{crit}$ (nm) | UVA/UVB ratio |
|---|---|---|
| C-10 | 389-390 | 1.017 |
| C-15 | 389-390 | 1.066 |
| C-20 | 389-390 | 1.044 |

Moreover, almost every cream has a UVA/UVB ratio higher than 0.90 (Table 4)—again the exception is sample C01 (UVA/UVB=0.570)—for the absorption characteristics described above. In particular, samples H15, H20, C10, C15 and C20 have values very close to 1; this means they can offer an effective comparable protection over the UVA range as well as UVB. Using the Boots Star Rating classification system, developed by Boots, one of the UK's main sunscreen producers and retailers, these creams would be rated as 5 stars, offering the maximum UVA protection (A. Springsteen, R. Yurek, M. Frazier, K. F. Carr, Anal. Chim. Acta, 1999, 380, 155).

Although these tests were not performed following exactly the COLIPA protocol, data reported here already give a very clear indication about the effectiveness of these creams as sunscreens. In fact, literature data shows that parameters such as the critical wavelength and the UVA/UVB ratio are weakly affected by experimental conditions, such as the nature of the substrate and the thickness of the cream layer used in the UV spectra measurements (D. Garoli, M. G. Pelizzo, B. Bernardini, P. Nicolosi, M. Alaibac, J. Dermat. Sci., 2008, 52, 193).

Figure 7C:
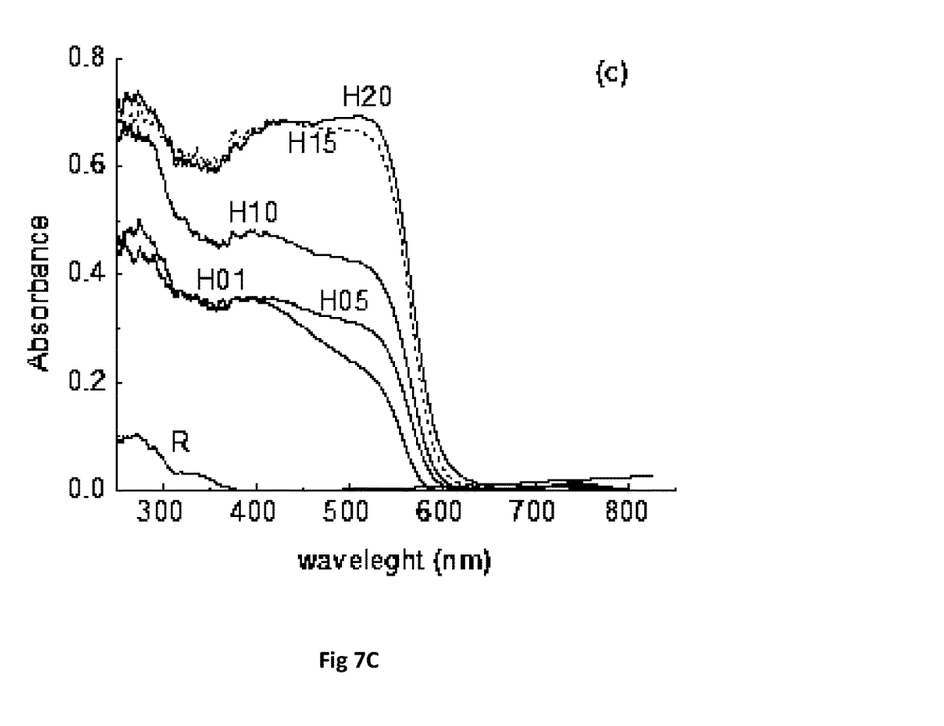
Figure 7D:
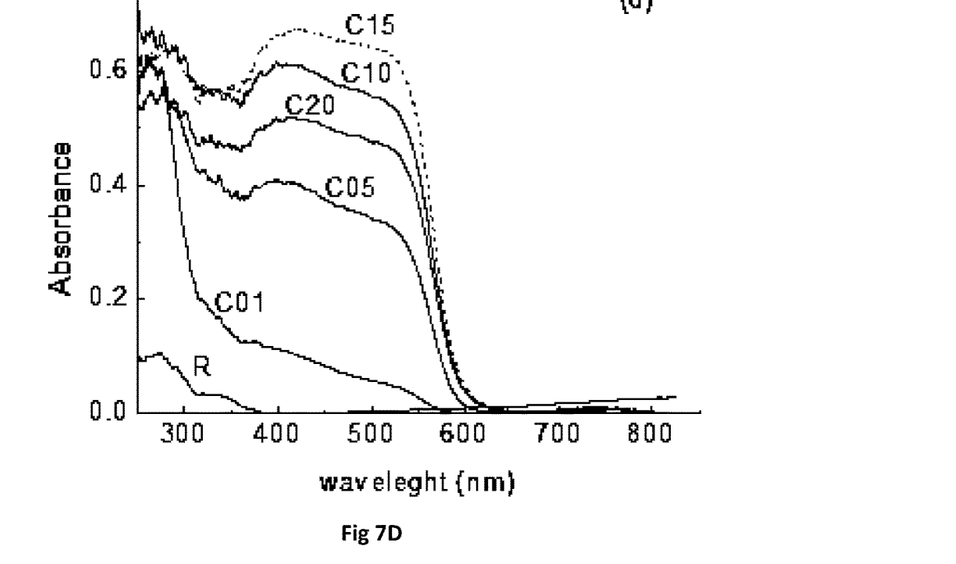

To test the photostability of the creams, they were irradiated and then assessed again, as described in the experimental section; the acquired UV spectra are shown in FIGS. 7(c) and 7(d), respectively. It can be seen that for both sets of samples, there are few changes in their absorption behaviour; in fact in all cases the absorption profile is not affected by the light irradiation. A decrease in the absorption intensity, however, was observed in some of the irradiated samples. The smaller absorption may be due to an increase in the crystallite size induced by the irradiation.

To quantify the decrease, the AUCI, $AUCI_A$ and $AUCI_B$ ratios were evaluated (see Table 5). In all cases the indexes were higher than 0.80, a value which is normally considered a stability indicator (D. Garoli, M. G. Pelizzo, B. Bernardini, P. Nicolosi, M. Alaibac, J. Dermat. Sci., 2008, 52, 193.) this was observed for the whole UV range, for the UVA and for the UVB subintervals. Moreover, for all creams the irradiation did not cause any change in the value of the critical wavelength $\lambda_{crit}$. These data clearly indicate the photostability of these samples.

TABLE 5

AUCI, $AUCI_A$ and $AUCI_B$ values for the creams.

| Sample | AUCI | $AUCI_A$ | $AUCI_B$ |
|---|---|---|---|
| H-01 | 0.986 | 0.956 | 0.998 |
| H-05 | 0.956 | 0.895 | 0.999 |
| H-10 | 0.828 | 0.823 | 0.898 |
| H-15 | 0.914 | 0.934 | 0.988 |
| H-20 | 0.919 | 0.927 | 0.999 |
| C-01 | 0.882 | 0.900 | 0.996 |
| C-05 | 0.984 | 0.999 | 0.903 |
| C-10 | 0.866 | 0.877 | 0.935 |
| C-15 | 0.873 | 0.898 | 0.946 |
| C-20 | 0.919 | 0.941 | 0.999 |

A test of acute irritation potential was performed to check whether these creams can be tolerated by the skin, without the active compounds causing any irritant reaction. The cream considered for the test was H-15; this was chosen because of its high absorbance, UVA/UVB ratio and irradiation stability.

Figure 8:
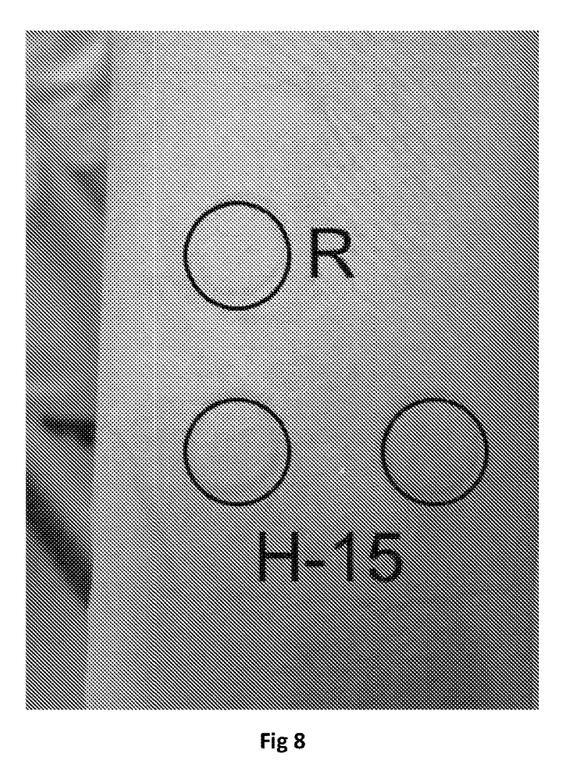
FIG. 8: Picture of the areas of the skin tested with the creams. Schematic representation of a preferred embodiment where:
(1) R represents the finn chamber with reference cream R, and
(2) H-15: Finn chambers with sample H-15.

FIG. 8 shows a picture of the area of the skin in contact with the cream. It can be seen that no irritation or erythema formation could be detected. Indeed, the part of the skin in contact with sample H-15 has the same appearance of the part in contact with reference sample R. Considering the score system used to evaluate the skin reaction, this corresponded to a 0 score. The same behaviour, and therefore 0 score, was observed for all 20 volunteers tested.

These products are not cause any irritant reaction in healthy people, and that they could be safely used. This study proves that also their interaction with cream matrix compounds can be considered safe.

Flow diagrams of particular embodiments of the presently disclosed methods are depicted in figures. The flow diagrams do not depict any particular means, rather the flow diagrams illustrate the functional information one of ordinary skill in the art requires to perform said methods required in accordance with the present disclosure.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

The disclosure is of course not in any way restricted to the embodiments described and a person with ordinary skill in the art will foresee many possibilities to modifications thereof without departing from the basic idea of the disclosure as defined in the appended claims.

The above described embodiments are obviously combinable.

The following dependent claims set out particular embodiments of the disclosure.

The invention claimed is:

1. A hydroxyapatite-based compound, comprising $Ca_9FeH(PO_4)_7$ and the hematite form of $\alpha$-$Fe_2O_3$, wherein the hydroxyapatite-based compound is a multiphasic compound in which hydroxyapatite and $Ca_9FeH(PO_4)_7$ are separate phases of the hydroxyapatite-based compound, and wherein the hydroxyapatite-based compound protects skin against UV radiation.

2. A composition comprising a therapeutically effective amount of the hydroxyapatite-based compound of claim 1, and a suitable amount of excipients in the form of a topic formulation.

3. The composition of claim 2, wherein the concentration of the hydroxyapatite-based compound in the composition is between 1-30% w/v.

4. The composition of claim 2, wherein the concentration of the hydroxyapatite-based compound in the composition is between 5-25% w/v.

5. The composition of claim 2, wherein the concentration of the hydroxyapatite-based compound in the composition is between 10-20% w/v.

6. The composition of claim 2, further comprising at least one of an emulsifier, a stabilizer, a thickener, dyes, fragrances, and a preservative.

7. The composition of claim 2, further comprising at least one emulsifier selected from the group consisting of polyglyceryl-3 methylglucose distearate and stearic acid.

8. The composition of claim 2, further comprising xantham gum as a thickener.

9. The composition of claim 2, further comprising glycerine.

10. The composition of claim 2, wherein the topic formulation is a cream.

11. The composition of claim 2, wherein the topic formulation is a water-oil emulsion.

12. The compound of claim 1, wherein the compound is at least one of a UVA sunscreen agent and a UVB sunscreen agent.

* * * * *